(12) United States Patent
Walzman

(10) Patent No.: US 10,342,573 B1
(45) Date of Patent: *Jul. 9, 2019

(54) SYSTEM AND METHOD FOR CLOT AMELIORATION

(71) Applicant: Daniel Ezra Walzman, Bergenfield, NJ (US)

(72) Inventor: Daniel Ezra Walzman, Bergenfield, NJ (US)

( * ) Notice: Subject to any disclaimer, the term of this patent is extended or adjusted under 35 U.S.C. 154(b) by 51 days.

This patent is subject to a terminal disclaimer.

(21) Appl. No.: 15/732,955

(22) Filed: Jan. 16, 2018

(51) Int. Cl.
*A61B 17/3207* (2006.01)
*A61B 17/00* (2006.01)
*A61M 25/10* (2013.01)

(52) U.S. Cl.
CPC ............... *A61B 17/320758* (2013.01); *A61B 2017/00477* (2013.01); *A61B 2017/320716* (2013.01); *A61B 2217/005* (2013.01); *A61B 2217/007* (2013.01); *A61M 25/10* (2013.01)

(58) Field of Classification Search
CPC .. A61B 17/320758; A61B 2017/00477; A61B 2017/320716; A61B 2217/005; A61B 2217/007; A61M 25/10
See application file for complete search history.

(56) References Cited

U.S. PATENT DOCUMENTS

| 5,540,707 A * | 7/1996 | Ressemann .... A61B 17/320725 604/22 |
| 6,454,775 B1 * | 9/2002 | Demarais ....... A61B 17/320725 606/128 |
| 8,043,313 B2 * | 10/2011 | Krolik .............. A61B 17/22032 604/99.01 |
| 2016/0151112 A1 * | 6/2016 | Ku ........................ A61B 18/18 606/41 |

* cited by examiner

Primary Examiner — Lauren P Farrar

(57) ABSTRACT

A treatment of a medical difficulty associated with the formation or presence of a blood clot in a blood vessel, commonly known as "thrombectomy." Said treatment may be achieved by introducing and positioning through a single lumen a device capable of macerating, irrigating and aspirating as well as supporting structures proximal to the distal end of said device. Said device is introduced via a blood vessel, and deployed at a treatment site. The macerator is then operated to dislocate thrombus, clot, or other occlusive materials at the target site, the irrigating element is then operated to continue to dislocate thrombus, clot, or other occlusive materials at the target site, and the aspirating element is used to collect and remove the disruptive materials from the target site.

8 Claims, 4 Drawing Sheets

SYSTEM AND METHOD FOR CLOT AMELIORATION

BACKGROUND OF THE INVENTION

Field of the Invention

The present invention relates generally to medical devices and methods. Specifically, the present invention teaches devices and methods for using a medical system for macerating, irrigating and aspirating, also capable of supporting structures proximal to the distal end of said device, for dislocating and removing occlusive material from blood vessels and other body lumens.

Discussion of the Prior Art

Thrombectomy is a medical treatment associated with the removal of occlusive material from blood vessels and other body lumens. Generally, removal of occlusive material from blood vessels and other body lumens is usually achieved by mechanically disrupting the clot. The disrupted thrombus or clot is then withdrawn through a catheter, typically with a vacuum or mechanical transport device. Most often a thrombus is removed from a blood vessel, as a part of a surgery to restore circulation to the affected part. Said surgery may include a longitudinal incision made into the blood vessel, and the clot is removed. Said surgery shortcomings include maintaining blood pressure and further clotting.

An alternative to surgery is anticoagulant therapy which is usually achieved by the introduction of thrombolytic agents. Said therapy is generally not effective in emergency situations due the amount of time (from several hours to several days) said therapy takes to work. The present invention overcomes the short coming of said surgery and said therapy by ameliorating incisions and executing the procedures in minutes.

The prior art teach the use of thrombectomy procedures the use of rotating blades, however they present a significant risk of injury to the blood vessel wall. Alternatively, those which rely primarily on vacuum extraction together with minimum disruption of the thrombus, often fail to achieve sufficient thrombus removal.

Thus, it is advantageous to provide improved device and method for performing thrombectomy procedures. The present invention provides a device and a method for use of said device which is capable of effective clot removal while minimizing the risk of injury to the blood vessel wall. The methods and procedures of the present invention with macerating, irrigation and aspirating element suitable for dislocating thrombus, clot, or other occlusive materials at treatment sites using the maceration and optional rotating element and the irrigation element, and collecting and removing the disruptive materials from the target site using the aspirating element. The device incorporates several separate devices normally delivered separately the prior art has taught into a single device, thus making thrombectomy procedures faster, cheaper and more effective. Furthermore, the device and associated methods describe how to effectively simultaneously use techniques that were previously thought to be effective when used separately.

SUMMARY OF THE INVENTION

The present invention provides a device which may be deployed via a single lumen of a delivery catheter/sheath and capable of macerating with the distal end, irrigating from the distal end and aspirating from the distal end of said delivery catheter/sheath, and method for removing occlusive material from body lumens. The present invention is advantageous when compared to the prior art for effective removal of the occlusive material from the body lumen. In particular, the macerating element is the end of a lumen introduces coaxially into said first single lumen, which allows irrigation and maceration from the distal end of said lumen, thus it does not require a separate wire or cutting element and does not require blades, and thereby eliminates the necessity of separate maceration device as well as the time necessary to deploy it, and the necessity of blades thus while minimizing the risk of injury to the blood vessel wall. Alternatively, it may eliminate the need for an addition catheter lumen for irrigation.

As described in detail below, the present invention employs both a lumen with a distal end capable of expansion and retraction, as well as rotating when desired, and irrigating for macerating or "dislocating" the thrombus, clot, or other occlusive material, when said lumen distal end is deployed proximally to a target site. The combined use of a single device to both mechanically macerate without blades and irrigate eliminates the necessity for precise positioning and minimizes or prevents contact between the present invention and the vessel/tissue wall, thus reducing or eliminating the potential for injury to the luminal wall. It should be noted that prior art such as U.S. Pat. No. 6,454,775 to Denise Demarais et al. (requires the maceration element to be carefully positioned ("the macerator is carefully positioned to minimize or prevent contact with and reduce or eliminate the potential for injury to the luminal wall"—see last sentence in SUMMARY OF THE INVENTION).

The present invention is nonobvious for multiple reasons. Prior art teaches that when using aspiration, resistance to flow through an aspirating tube is inversely proportional to the fourth power of the radius, according to Poiseuille's equation;

$$R \propto \frac{\eta L}{r^4}$$

Therefore, if one decreases the effective radius of the aspirating catheter by introducing another device into it, the result will be a disproportionate increase in resistance to flow, and consequential decrease in flow. Therefore, it is counterintuitive to add said second device to enhance effective aspiration of clot and/or debris. Additionally, other efforts to incorporate irrigation into thrombectomy systems have been complicated by the irrigation encouraging dislodgement of debris and downstream emboli, so it has become counterintuitive to add said irrigation. The present invention ameliorates the limitations of the prior art by adding simultaneous aspiration, to capture and remove any such dislodged debris. Indeed, in some applications, the present invention teaches to combine the flow arrest proximal to the aspiration with active irrigation to create an effectively closed flow-reversal circuit to facilitate debris removal and prevent unwanted emboli. The active irrigation also prevents vessel collapse and/or an empty vacuum, both of which will prevent flow, if flow arrest and aspiration are applied together without said irrigation. Furthermore, we add maceration which allowed freer flow of the debris, by breaking said debris into smaller pieces, to overcome the limitations of the increased resistance to flow we introduce. Additionally, prior art has avoided use of irrigation, often for fear of undue vessel expansion that can result in vessel rupture. The current invention prevents excessive vessel expansion by using simultaneous aspiration. If desired this can be further monitored actively by using a combination of contrast in the irrigant, and irrigating under fluoroscopic guidance, so irrigation can be stopped if it is seen to be overcoming the aspiration.

The present invention comprises system with a single lumen with a proximal end and a distal end. There are additional coaxial lumina within said single lumen. Said system comprises a catheter body having a proximal end located outside of a patient, and a distal end which is designed to move inside a patient. Said distal end may be angled and rotated using communication from said proximal end. In some embodiments it can be straight. In some embodiments it can have a complex shape. In some embodiments it can be sinusoidal. An expansible element may be deployed from a position near the distal end due to a communication from said proximal end. The present invention is capable of irrigating a target site and aspirating a target site using elements introduced through the same single lumen. The most outer concentric lumen is most often used for aspiration, while the most innermost concentric lumen is most often used for irrigation. Said distal end is capable of rotating in a helical or other shape to start to dislocate the occlusive material and said distal end may simultaneously irrigate the target site. Said distal end macerator is configured to disrupt occlusive material after a target site support element, such as a balloon is deployed to prevent the macerated material from moving away from the target site. Simultaneously, said distal end will aspirate said macerated material away from the target site and deliver it out of a hole near said proximal end. Additionally, in alternative from the rotational maceration, said distal end may contain a macerator that can be radially expansile, and can macerate via sequential radial expansion and contracting. With each cycle the wires of the macerator break up the clot. When desired, small changes in the location of the macerator can effectuate additional clot maceration as well. In such embodiments the macerator is a wire capture weaved coil or stent on the outside of the distal-most segment of the inner-most lumen, in which said wire capture device is attached at its end in a fixed fashion to said inner-most lumen/hypotube. The inner-most lumen is further contained within an intermediate lumen. The length of said intermediate lumen ends so that the unexpanded wire capture device spans the distance from its attachment to the inner-most lumen/hypotube to the distal end of said intermediate lumen, to which the proximal end of said capture device is permanently affixed as well. The inner-most lumen can be moved longitudinally relative to the intermediate lumen. When the innermost lumen is pulled back relative to the intermediate lumen, to shorten the distance between the ends of both lumens, the wire capture device is foreshortened, causing it to radially expand. Said wire capture device can thus be serially shortened/expanded and lengthened/unexpanded. Each time this is done said wires course through the debris/clot, thereby macerating said debris/clot into smaller pieces. In some embodiments there are additional side-holes along the length of said inner-most lumen that overlaps with the position of said capture device, allowing simultaneous irrigation into and distal to said debris.

The prior art does not teach the use of a single lumen which comprises both an, irrigation and aspiration element, with the exception of disclosures for a rotating separator, irrigator microcatheter for thrombectomy (application Ser. No. 15/258,877 filed Sep. 7, 2016 which was abandoned but used as priority for both Ser. No. 15/731,478 filed Jun. 16, 2017 and Ser. No. 15/530,898 filed Mar. 20, 2017 by the inventor of the present invention).

As in the case of devices and method taught by the prior art the dislocated material may be removed through the catheter lumen by aspiration using an external vacuum source and/or a mechanical pump.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

Figure 1:
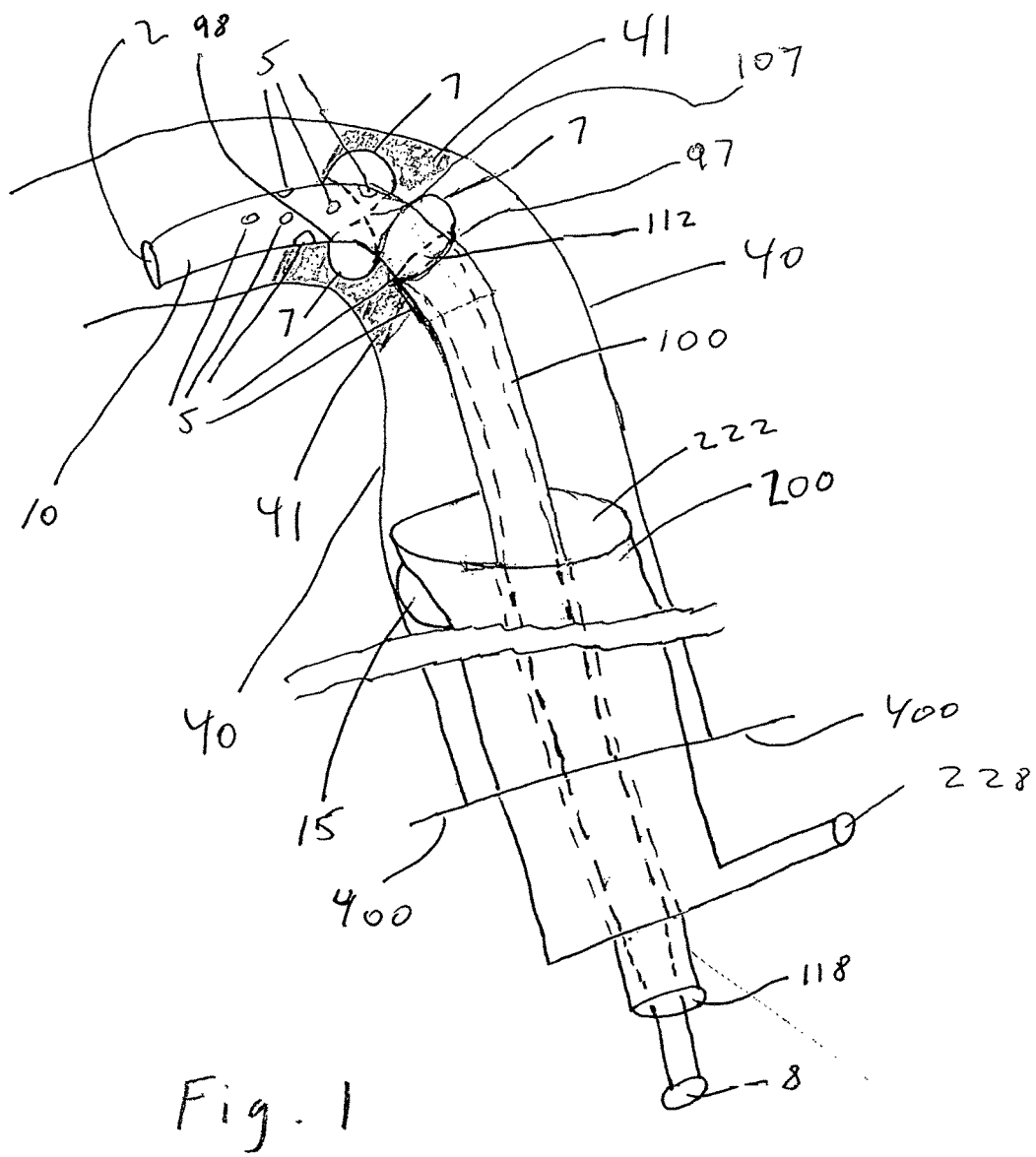
FIG. 1 is a cutaway view of the preferred embodiment of the current invention partially disposed within a blood vessel, displayed in use.

Referring now to FIG. 1, the present invention is disposed within vessel walls (40) and has impaled obstruction (41), typically a clot. The current invention is composed of three concentric sheaths, namely inner sheath (10), intermediate sheath (100), and outer sheath (200).

The first, innermost sheath is a hypotube (10) having a distal tip (2), a proximal tip (8), at least one perforation (5), and macerating elements (7). Proximal tip (8) communicates with an irrigation control system (not shown) to deliver irrigating fluid therethrough to perforations (5). Macerating elements (7) may be at least one wire or at least one stent attached to inner hypotube (10) at connection points (98). Macerating wire loops (7) are depicted in the embodiment illustrated. Obscured wires or loops (107) are depicted passing behind inner hypotube (10) as dotted lines to shown rotation. In some embodiments inner hypotube (10) may have an attached wire (not shown) extending from its distal end (2).

The second sheath is intermediate hypotube (100). Inner hypotube (10) is disposed within intermediate hypotube (100). Intermediate hypotube (100) has a distal aperture (112) and a proximal end (118). Distal aperture (112) is affixed to macerating element (7) at attachment point (97) located on the rim of distal aperture (112). Proximal end (118) communicates with a user control device (not shown) external to the device-body interface (400), capable of moving inner hypotube (10) longitudinally through intermediate hypotube (100).

The outermost third sheath (200) is wedged within vessel wall (40). Sheath (200) has a distal opening (222) and a proximal opening (228). Distal opening (222) is adapted to aspirate debris; proximal opening (228) communicates with an aspiration control device (not shown) located outside the body. If wedging within vessel wall (40) is not desired, optional inflatable balloon (15) may be deployed to minimize or eliminate blood flow within the vessel.

Figure 2:
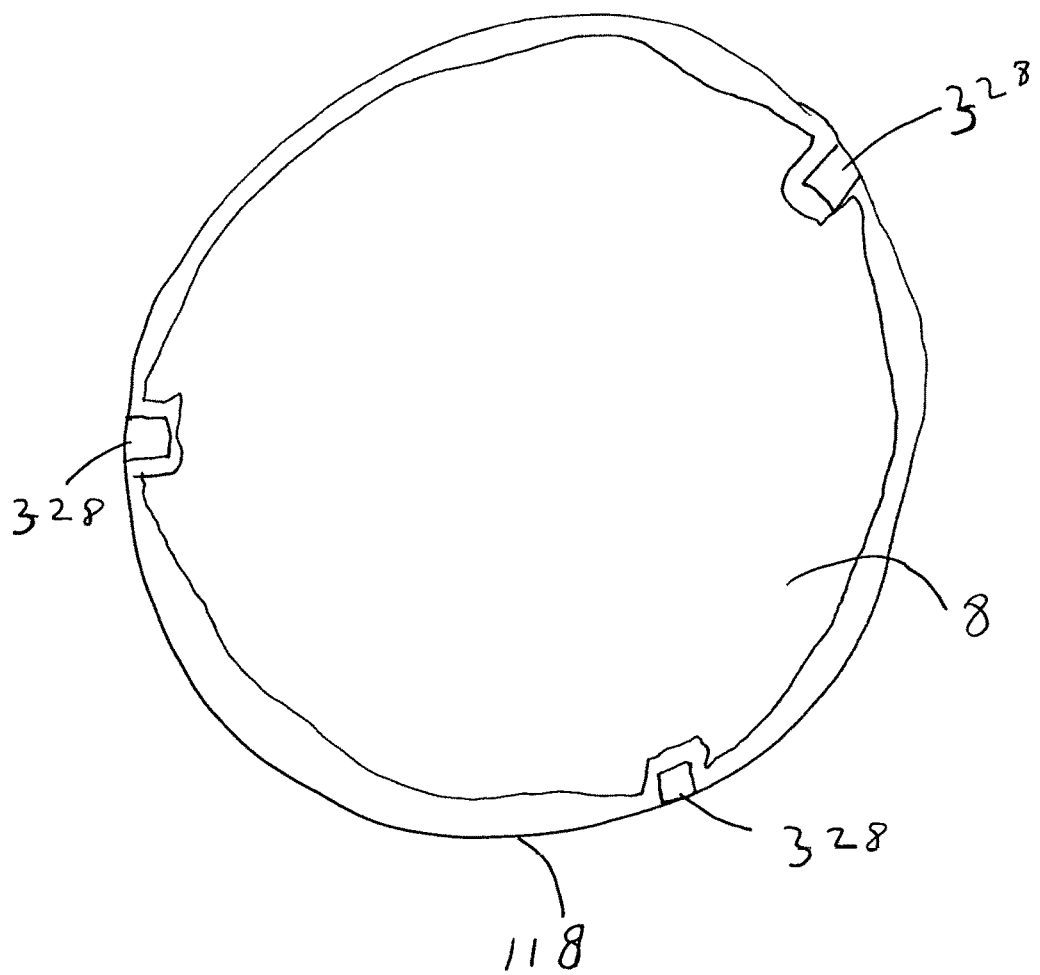
FIG. 2 displays a cross-sectional view of an inner hypotube disposed within an intermediate hypotube, highlighting one embodiment of interlocking elements adapted to prevent radial rotation relative to each other while allowing translational extension of the inner hypotube longitudinally.

In operation, inner hypotube (10) is translated longitudinally, sliding within intermediate hypotube (100). Inner hypotube (10) is designed for slidable, longitudinal extension to a set distance beyond the rim of distal aperture (112). Referring to FIG. 2, proximal tip (8) of inner hypotube (10) and proximal end (118) of intermediate hypotube (100) are linked by interlocks (328). Interlocks (328) force inner hypotube (10) to rotate in the same manner as intermediate hypotube (100) without interfering with longitudinal extension. The purpose of interlocks (328) is to ensure that inner hypotube (10) and intermediate hypotube (100) do not rotate independently relative to each other. This allows for effective rotation of the wire loops/stent (7) when desired, to aid in maceration.

Figure 3:
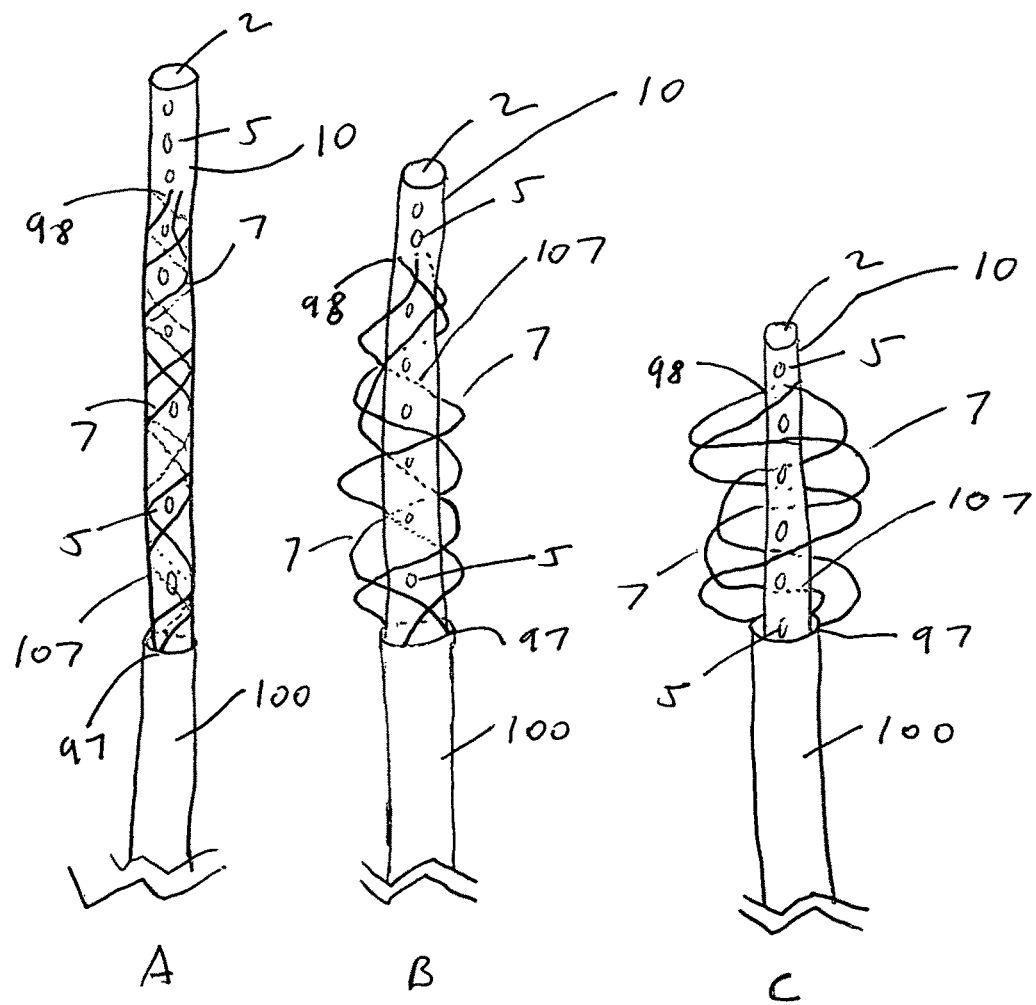
FIG. 3 shows the maceration element of the current invention disposed in collapsed, partially expanded, and fully expanded mode.

Referring to FIG. 3, the distal end of the invention is shown in three positions. Position A shows maceration element (7) in a collapsed state. Position B shows maceration element (7) partially expanded. Position C shows maceration element (7) fully expanded. In positions A, B and C, macerating element (7) is attached to two points. It is attached distally to inner hypotube (10) at point (98) and proximally to intermediate hypotube (100) at attachment point (97) at the rim. Also, in all positions, perforations (5) are located distally to point (98) and proximally to attachment point (97), as well as areas therebetween. This configuration allows irrigation before, at and after the targeted obstruction or clot (41). Macerating stent or wire (7) expands away from inner hypotube (10) and toward vessel wall (40) when point (98) on inner hypotube (10) is pulled toward attachment point (97) on intermediate hypotube (100). The contraction forces macerating stent or wire (7) outward radially.

Conversely, moving point (98) away from attachment point (97) will cause the contraction of macerating wire (7) until fully collapsed.

It should be noted that in positions A, B and C that the wires (7) are all connected to the inner hypotube as well as to the intermediate hypotube, as such (107) represents the position of wires (7) behind inner hypotube (10).

It should be noted further that the expansion of macerating stent or wire (7) into blockage (41) can affix blockage (41) onto macerating element (7), thus capturing blockage (41) by the present invention. Once blockage (41) is captured, it may simply be withdrawn from the vessel with walls (40) by withdrawing the device of the current invention beyond device/body interface (400), if there is residual clot after maceration, irrigation, and aspiration are effectuated.

Figure 4:
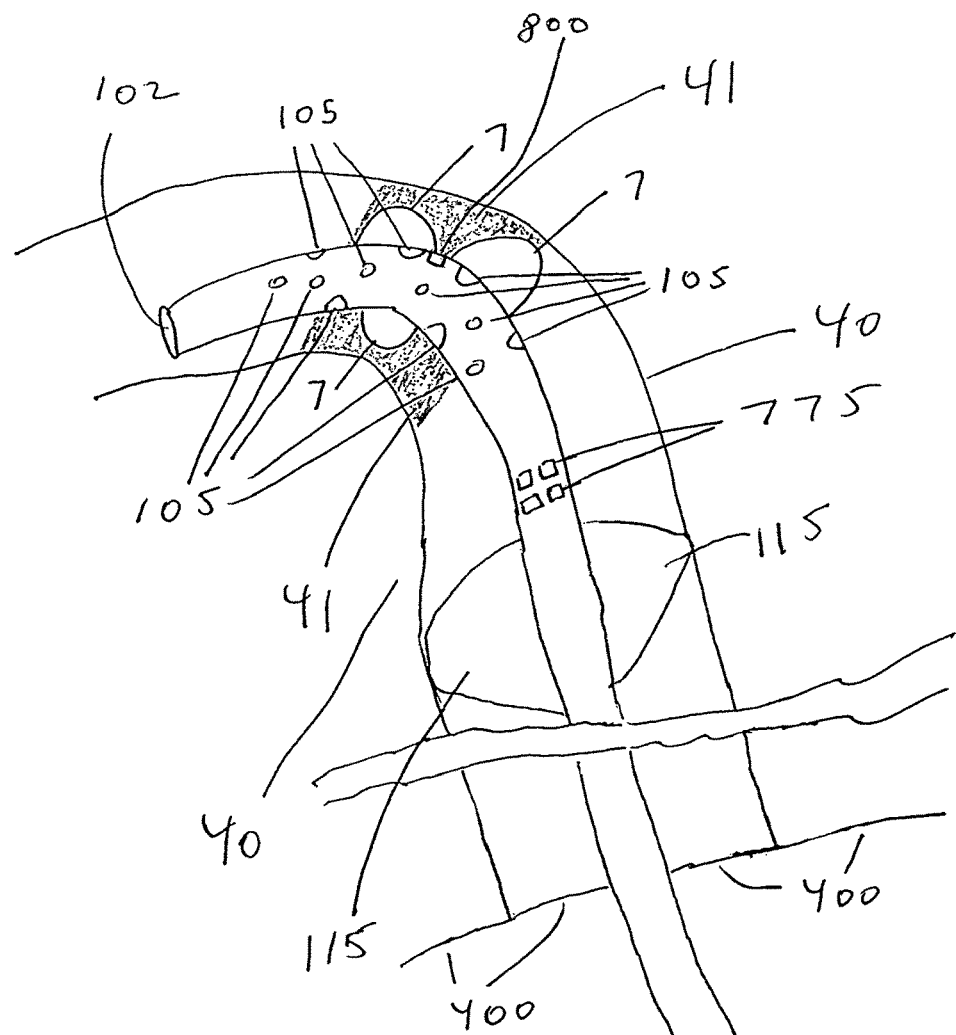
FIG. 4 is an optional embodiment, a multilayered single lumen embodiment in use.
Figure 4:
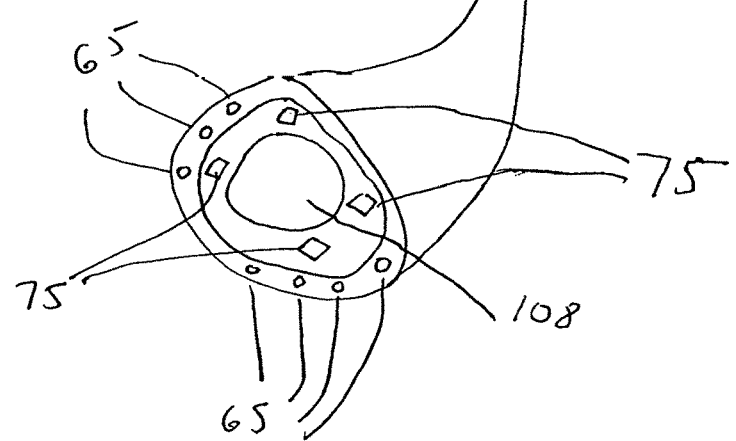

Referring now to FIG. 4, is an alternate embodiment wherein the entire device is incorporated into a multichanneled single lumen having a proximal end (108) and distal end (102). Rather than having a separate sheath for aspiration, such as (200) in FIG. 1, the alternate embodiment of FIG. 4 employs at least one balloon (115) proximally to distal aspiration openings (775). Distal aspiration openings (775) are distal to proximal aspiration openings (75) and communicate with proximal aspiration openings (75) through internal lumens. Said communication allows the present invention to aspirate dislocated elements of clot (41). Not shown is the aspiration control element connected to proximal aspiration openings (75). Additionally, perforations (105) communicate with proximal irrigation elements (65) through internal lumens to allow irrigation via the irrigation control element (not shown). At least one slit (800) is provided to allow at least one macerating element (7) to emerge. It should be noted that the lumen is composed of multiple layers of elastic material capable of rotating and extending separate channels longitudinally.

It will be understood that the above particular embodiments are shown and described by way of illustration only. The principles and the features of the present disclosure may be employed in various and numerous embodiments thereof without departing from the scope and spirit of the disclosure as claimed. The above-described embodiments illustrate the scope of the disclosure but do not restrict the scope of the disclosure.

What is claimed is:

1. A medical device for ameliorating thrombi, comprising at least three channels including embedded lumens adapted for insertion into a blood vessel, comprising:
   (a) an inner channel,
      including, a proximal tip, a distal tip, and at least one macerating element capable of both expanding and collapsing;
      at least one distal irrigation element adapted to irrigate a blockage, and
      at least one proximal opening irrigation element communicating via a dedicated lumen, terminating at an irrigation source outside a patient's body;
   (b) an intermediate channel,
      including a distal aperture and a proximal end;
      wherein said at least one macerating element is affixed to said inner channel at at least one connection point, and attached to said intermediate channel at an attachment point; and
      including at least one distal aspiration opening adapted to aspirate debris, and at least one proximal aspiration opening communicating via at least one dedicated lumen, terminating at an aspiration control device outside said patient's body,
   (c) an outer sheath,
      including at least one distal hole adapted to aspirate debris via said at least one distal aspiration opening, and at least one proximal opening hole communicating via at least one dedicated lumen, terminating at said aspiration control device,
      and at least one slit to allow said at least one maceration element to emerge from said inner channel through said intermediate channel and said outer sheath toward a wall of said blood vessel;
      wherein said outer sheath is disposed within said blood vessel, having said at least one distal opening hole adapted to aspirate debris and said at least one proximal hole communicating with said aspiration control device;
      wherein said intermediate channel slides along the exterior surface of said inner channel,
      wherein said inner channel and said intermediate channel are adapted to rotate together 360°, and
      wherein said inner channel and said intermediate channel incorporate an interlocking element adapted to prevent rotation of said inner channel relative to said intermediate channel, as well as to facilitate the longitudinal movement of said inner channel.

2. The medical device of claim 1, further including at least one balloon disposed proximally to said at least one distal hole.

3. The medical device of claim 1, said distal tip further including at least perforation;
   wherein said perforation is adapted to irrigate said blockage, and said proximal tip communicates via said dedicated lumen terminating at said irrigation source outside said patient's body, and wherein said at least one perforation is disposed distally to said at least one connection point and proximally to said attachment point and areas therebetween, said at least one perforation and said distal tip communicate by said dedicated lumen with said proximal tip to allow injection of fluid therethrough from outside said patient's body.

4. A method for ameliorating a blockage of an artery using the device of claim 1, comprising the steps of:
   (a) inflating a balloon to occlude blood flow proximally to said blockage,
   (b) disrupting said blockage by mechanical maceration, and
   (c) alternating irrigation and aspiration proximally to said blockage to remove liberated debris.

5. The method of claim 4, wherein said blockage is a thrombus.

6. The method of claim 4, wherein said blockage is an embolus.

7. The method of claim 4, wherein said blockage is stenosis.

8. A method for ameliorating clots in a blood vessel using the device of claim 1, comprising the steps of:
   (a) inserting distal end of said device in said blood vessel;
   (b) moving said device longitudinally along said blood Vessel until at least one perforation is distal to a target area, and at least one maceration element is disposed within said target area;
   (c) deploying said at least one maceration element;
   (d) rotating said at least one maceration element;
   (e) activating fluid infusion via said at least one perforation;
   (f) aspirating using outer sheath;
   (g) terminating rotation of said at least one maceration element;
   (h) retracting said at least one maceration element;
   (i) deactivating said fluid infusion;
   (j) deactivating aspiration; and
   (k) withdrawing said medical device from said blood vessel.

* * * * *